United States Patent [19]

Balasubramanyam et al.

[11] Patent Number: 6,160,172
[45] Date of Patent: Dec. 12, 2000

[54] SOLUBLE DOUBLE METAL SALT OF GROUP IA AND IIA OF (-) HYDROXYCITRIC ACID, PROCESS OF PREPARING THE SAME AND ITS USE IN BEVERAGES AND OTHER FOOD PRODUCTS WITHOUT EFFECTING THEIR FLAVOR AND PROPERTIES

[75] Inventors: Karanam Balasubramanyam; Bhaskaran Chandrasekhar; Candadai Seshadri Ramadoss; Pillarisetti Venkata Subba Rao, all of Bangalore, India

[73] Assignee: Vittal Mallya Scientific Research Foundation, Bangalore, India

[21] Appl. No.: 09/059,354

[22] Filed: Apr. 14, 1998

[30] Foreign Application Priority Data

Aug. 27, 1997 [IN] India ............................. 1881/MAS/97
Aug. 27, 1997 [IN] India ............................. 1880/MAS/97
Sep. 8, 1997 [IN] India ............................. 1986/MAS/97
Sep. 8, 1997 [IN] India ............................. 1987/MAS/97
Sep. 8, 1997 [IN] India ............................. 1985/MAS/97

[51] Int. Cl.$^7$ .................................................. C07C 59/265
[52] U.S. Cl. ...................... 562/584; 514/574; 568/579; 568/580; 568/590
[58] Field of Search ............................ 514/574; 568/579, 568/580, 590; 562/584

[56] References Cited

U.S. PATENT DOCUMENTS

| | | | |
|---|---|---|---|
| 3,764,692 | 10/1973 | Lowenstein ............................. | 514/449 |
| 3,767,678 | 10/1973 | Guthrie et al. ........................... | 549/243 |
| 3,810,931 | 5/1974 | Guthrie et al. ............................. | 558/52 |
| 4,275,234 | 6/1981 | Baniel et al. ............................ | 562/584 |
| 4,643,902 | 2/1987 | Lawhon et al. ......................... | 426/271 |
| 5,656,314 | 8/1997 | Moffett et al. .......................... | 426/271 |

FOREIGN PATENT DOCUMENTS 96-13094 10/1996 France .

OTHER PUBLICATIONS

Y.S. Lewis, Isolation and Properties of Hydroxycitric acid, Methods in Enzymology; vol. XIII, pp. 613–617, Oct. 1969.

*Primary Examiner*—Paul J. Killos
*Assistant Examiner*—Taylor Victor Oh

*Attorney, Agent, or Firm*—Jones Jain, L.L.P.; Chittaranjan N. Nirmel; Mishrilal Jain

[57] ABSTRACT

The present invention is directed to a new soluble double metal salt of group IA and IIA of (–) hydroxycitric acid of general formula I:

where X is IA group metal: Li or Na or K or Rb or Cs or Fr where Y is IIA group metal: Be or Mg or Ca or Sr or Ba or Ra where the concentration of X in the salt varies from 1.5–51.0%, the concentration of Y in the salts varies from 2.0–50.9%, the concentration of HCA in the salt varies from 31.0–93.0% depending on the nature of X and Y.

This invention more particularly relates to new soluble double metal salt of group IA and IIA of (–) hydroxycitric acid of general formula II.

This invention also includes a process of preparing the soluble double metal salt of group IA and IIA of (–) hydroxycitric acid of general formula I comprising: preparing (–) hydroxycitric acid liquid concentrate/solid lactone of hyroxycitric acid from Garcinia extract, neutralizing the free (–) hydroxycitric acid present in the said (–) hydroxycitric acid liquid concentrate/solid lactone (–) hydroxycitric acid with group IA metal hydroxides, displacing partially the group IA metal ions in the above salt solutions by adding group IIA metal chlorides to form soluble double metal salt of group IA and IIA of (–) hydroxycitric acid, precipitating the said double metal salt of group IA & IIA of (–) hydroxycitric acid by adding aqueous polar solvent to get soluble IIA metal salt of (–) hydroxycitric acid or obtaining the soluble double metal salt as powder by spray drying prior to the solvent addition or spray drying water solubilised solvent precipitated material.

The instant invention also discloses the use of the said soluble double metal salt of group IA and IIA of (–) hydroxycitric acid of formula I and particularly formula II in beverages and other food products and its use in beverages and other food products.

10 Claims, No Drawings

SOLUBLE DOUBLE METAL SALT OF GROUP IA AND IIA OF (-) HYDROXYCITRIC ACID, PROCESS OF PREPARING THE SAME AND ITS USE IN BEVERAGES AND OTHER FOOD PRODUCTS WITHOUT EFFECTING THEIR FLAVOR AND PROPERTIES

This invention relates to a new soluble double metal salt of group IA and II A of (−) hydroxycitric acid, process of preparing the same and its use in beverages and other food products without effecting their flavor and properties. This product with >98% purity can be used safely not only as a food supplement in various nutriceutical formulations and beverages but also for effecting obesity control.

BACKGROUND (−) Hydroxycitric acid HCA) occurs in the fruit rind of Garcinia species (G. Cambogia, *G. indica* and *G. atroviridis*). The first two species grow abundantly in India and the third occurs mostly in South East Asian countries. The success of this natural food product derived from Garcinia fruit has been documented and been in use since several centuries BC. Also known as "Kokum", the extracts of the fruit have been used as a tart flavoring in meat and seafood dishes, turned into a refreshing beverage that serves as a unique flavor enhancer, gourmet spice and a digestive after a heavy meal. In Ayurveda, the traditional ancient system of herbal medicine in India, Garcinia is also considered to be one of the prime herbs that are beneficial for the heart.

In more recent times, Garcinia has received worldwide attention as a nutriceutical for effective obesity control. Several scientists including at Hoffman-La Roche have established that HCA, the active ingredient in the fruit, prevents the conversion of excess carbohydrates to fat in animals. The energy released by the excess carbohydrate is converted into and stored as glycogen, a readily usable form of energy. Interestingly, it has been shown to inhibit ATP dependent citrate-lyase, a key enzyme in diverting carbohydrate to fatty acids and cholesterol synthesis (Sullivan et al. Lipids, 9:121 and 129 (1973), Sergio, W., Medical Hypotehsis 27:39 (1988)).

The age-old practice of consuming Garcinia rind as a food additive by inhabitants of Malabar and Konkan coast of the Indian penisula has established the safety of HCA. The isolation and chemical nature of (−) hydroxycitric acid from Garcinia rind are described in the publication of Lewis Y. S., et al. (Methods in Enzymology, 13:613 (1967) and in the patents (Indian patents 160753 & 178298 and U.S. Pat. Nos. 5536516 & 5656314).

It is believed that consumption of HCA influences the body metabolism leading to the saturation of glycogen receptors in the liver and a consequent transmission of signals of satiation to brain. Even as a food supplement, (−) HCA helps a person to lose/control weight in a natural way without affecting normal physical activities.

In view of its unique property, several health care formulations incorporating HCA are being sold across the counter in the Western markets. These include tablets, capsules, herbal teas, chocolate bars, milk shakes and other beverages. The active ingredient (HCA) from this insoluble HCA salt is released upon contact with hydrochloric acid in the stomach and absorbed through the intestine to exert its metabolic effect.

There is prior art on the preparation of a soluble tripotassium salt of (−) HCA (Lewis Y. S., et al (Methods in Enzymology, 13:613 (1967), International Patent WO 96/36585, U.S. Pat. No. 08/440,968 filed). However, its alkaline nature and risks associated with the consumption of high potassium (~36%) makes this product unsuitable for HCA-based formulations.

In our earlier patents (Indian patent No. 178298 & U.S. Pat. Nos. 5536516, 5656314) which describes preparation of a concentrate of (−) hydroxycitric acid and its lactone in liquid form, comprising of several steps like water extraction of Garcinia rind containing (−) hydroxycitric acid and its concentration, acetone refinement of this concentrated water extract, evaporation of acetone, loading thus obtained refined extract on ion-exchange columns containing an anion exchange resin followed by a cation exchange resin, and finally evaporation of the free acid liberated from the ion-exchange process to said concentration. This liquid form of (−) hydroxycitric acid has problems of stability and half-life.

In addition, its highly acidic nature poses problems in formulating into beverage and various other food products without affecting their flavor and properties.

The object of this invention is to overcome the above drawbacks by developing a new soluble double metal salt of (−) hydroxycitric acid which will not pose any problem in formulating with beverages and various other food products without affecting their flavor and properties.

To achieve the said objective, this invention provides a new soluble double metal salt of group IA and II A of (−) hydroxycitric acid of general formula I and more particularly formula II as given below:

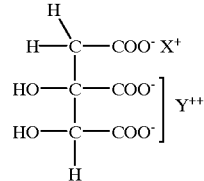

Formula I

Where X is IA group metal: Li or Na or K or Rb or Cs or Fr

Where Y is IIA group metal: Be or Mg or Ca or Sr or Ba or Ra where concentration of X in the salt varies from 1.5–51.0%, the concentration of Y in the salts varies from 2.0–50.9%, the concentration of HCA in the salts varies from 31.0–93.0% depending on the nature of X and Y.

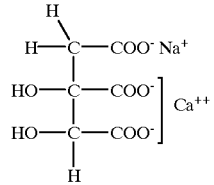

Formula II concentration of sodium in the salt: 8.58%,
concentration of calcium in the salt: 14.92%
concentration of (−) hydroxycitric acid: 76.50%, This invention further relates to a process for preparing the said soluble metal salt of group IA and IIA of (−)

hydroxycitric acid of general formula I or more particularly formula II comprising:

Step 1: preparing (−) hydroxycitric acid liquid concentrate/solid lactone of hydroxycitric acid from Garcinia extract, Step 2: neutralizing the free (−) hydroxycitric acid present in the said (−) hydroxycitric acid liquid concentrate/solid lactone present (−) hydroxycitric acid with group IA metal hydroxides Step 3: displacing partially group IA metal ions in the above salt solutions by adding group IIA metal chlorides to form soluble double metal salt of group IA and IIA of (−) hydroxycitric acid, Step 4: precipitating the said solubilised group IIA metal salts of (−) hydroxycitric acid by adding aqueous polar solvent to get soluble IIA metal salt of (−) hydroxycitric acid The free (−) hydroxycitric acid present in the step 2 is neutralized by three equivalents of group IA metal hydroxides.

Partial displacement of group IA metal ion in step 3 is carried out with one equivalent of group IIA metal chloride.

The soluble metal salt of hydroxycitric acid is obtained in powder from by spray drying prior to the solvent addition or spray drying water solubilised solvent precipitated material.

The said polar solvents are methanol, ethanol, propanol, isopropanol and acetone.

The (−) hydroxycitric acid concentrate in step 1 is prepared from the Garcinia extract by:
i) treating the said Garcinia extract with group IA metal hydroxide to obtain soluble group IA metal salt of (−) hydroxycitric acid,
ii) displacing completely the said group IA metal ions with group IIA metal ion by adding group IIA metal chlorides solution to precipitate insoluble group IIA metal salts of (−) hydroxycitric acid.
iii) collecting the said precipitate of insoluble group IIA metal salt of (−) hydroxycitric acid and washing it with water,
iv) adding a water soluble organic acid to the said precipitated insoluble group IIA metal salt of HCA to form a stronger salt of group IIA metal and release (−) hydroxycitric acid,
v) repeating the steps (iii) and (iv) to form concentrate of (−) hydroxycitric acid,
vi) decolorizing the said (−) hydroxycitric acid concentrate, if desired.

The water soluble organic acid used in step (iv) is an oxalic acid.

The (−) hydroxycitric acid concentrate in step 1 is also prepared from the Garcinia by:
i) extracting Garcinia rind with aqueous polar solvent and filtering,
ii) heating the filtrate in vacuum at 50–80° C. to evaporate the said polar solvent,
iii) removing the water insoluble substances to get the (−) hydroxycitric acid concentrate,
iv) decolorizing the said (−) hydroxycitric acid concentrate, if necessary.

The aqueous polar solvent used in step 1 is 80% acetone in water.

The (−) hydroxycitric acid concentrate in step 1 is also prepared from the Garcinia extract by:
i) loading the Garcinia extract containing free (−) hydroxycitric acid on anion exchange resin column,
ii) washing the said column with group IA metal hydroxide solution to get group IA metal salt of (−) hydroxycitric acid,
iii) loading the said group IA metal salt solution of (−) hydroxycitric acid on cation exchange resin to get free (−) hydroxycitric acid,
iv) heating the said free (−) hydroxycitric acid in vacuum to evaporate water and get the (−) hydroxycitric acid concentrate.
v) decolorizing the said (−) hydroxycitric acid concentrate, if necessary.

The said (−) hydroxycitric acid concentrate is decolorized by heating with 2–5% activated charcoal, if desired.

The said lactone of (−) hydroxycitric acid in step 1 is prepared by:
i) heating the (−) hydroxycitric acid concentrate at 67° C. to form syrup of (−) hydroxycitric acid lactone,
ii) drying and desiccating the said syrup to get solid mass of (−) hydroxycitric acid lactone.

A process for the preparation of soluble double metal salt of group IA and IIA of (−) hydroxycitric acid comprising:
i) loading Garcinia extract containing free (−) hydroxycitric acid on an anion exchange resin column,
ii) washing the said anion exchange resin column with Group IA metal hydroxide to obtain group IA metal salt of (−) hydroxycitric acid solution.
iii) treating the said group IA metal salt of (−) hydroxycitric acid partially with group IIA metal chloride to get soluble double metal salt of group IA and IIA of (−) hydroxycitric acid.

Group IA metal hydroxides used are LiOH, NaOH, KOH, RbOH, CsOH and FrOH.

Group IIA metal chlorides $BeCl_2$, $MgCl_2$, $CaCl_2$, $SrCl_2$, $BaCl_2$ and $RaCl2$.

The soluble double metal salt of group IA and IIA of (−) hydroxycitric acid is soluble sodium calcium salt of (−) hydroxycitric acid.

The process will now be described with reference to the following examples.

EXAMPLE 1

Water extract of Garcinia rind is obtained by counter current extraction, this is carried out in three vessels more specifically each time fresh Garcinia rind each time 1 Kg is loaded into vessel 3 and treated with 1.5 liters of water, the rind is moved from $V_3$ to $V_2$ then to $V_1$. On the other hand the extract was moved from $V_1$ to $V_2$ then to $V_3$.

The extract obtained starting from 3 Kgs of rind was 3.6 litres containing 620 gms of acid along with the other water-soluble substances. The total soluble constituents in the extract i.e. brix was found to be 43 degrees. The extraction efficiency was found to be 90%. This acid was transferred to a vessel and neutralized by addition if 358 gm of sodium hydroxide. After cooling this solution to room temperature, 500 ml of solution containing 490 gm of calcium chloride was added to it and resultant insoluble calcium salt was centrifuged and washed thoroughly to removed the color and water soluble impurities. The salt obtained was dried and weight is found to be 693 gm.

One hundred grams of this insoluble salt was taken in a one liter vessel to and 71.32 gm oxalic acid dihydrate dissolved in 350 ml of water was added and stirred at 150 RPM on a shaker for 30 min, and the supernatant 210 ml of was collected. To this supernatant 71.32 gm of oxalic acid dihydrate was added and another 100 gm of calcium hydroxycitrate added and this procedure is followed until the hydroxycitric acid content in the extract reaches −45% detected by high performance liquid chromatography HPLC). The traces of oxalic acid were also removed by finally adding excess calcium hydroxycitrate. This was monitored by HPLC by observing the total absence of oxalic acid peak. The solution of hydroxycitric acid thus obtained was found to contain 202 gm of acid in 450 ml of extract. This was neutralized by 117 gm of sodium hydroxide and the solution was cooled to room temperature. To this sodium salt solution of hydroxycitric acid, 200 ml of solution containing 81 gm of calcium chloride was added drop wise with vigorous stirring. The soluble calcium salt of hydroxycitric acid was then precipitated by addition of ethanol. Then precipitated salt was filtered, washed with ethanol and dried to obtain 234 gm of the soluble calcium salt of hydroxycitric acid (yield: 91.2%) In another experiment, the above procedure was repeated exactly after collecting the ethanol precipitated material. This was again dissolved in water to 30% and the material thus obtained was spray dried to obtain 243 gm of the soluble salt of hydroxycitric acid (yield 95%).

EXAMPLE 2

One hundred gm Garcinia Cambogia rind was extracted 4 times with 80% acetone in water (250 ml each time) for 4 hours. The combined extract (830-ml) was concentrated to 300 ml by heating in vacuo at 56° C. (500 millibar and filtered through cheese cloth to remove water insoluble non polar substances. The filtrate (260-ml) containing 18 gm of hydroxycitric acid decolorized by addition of 2.6 gm of activated charcoal and filtered. The resultant clear solution was concentrated to 50 ml, and the free acid was converted into the sodium salt of hydroxycitric acid by the addition of 11 gm of sodium hydroxide pellets, were added. To this formed solution of sodium salt of (−) hydroxycitric acid 20 ml of solution containing 9 gm of calcium chloride was added drop wise with vigorous stirring. The soluble salt of hydroxycitric acid is then precipitated by addition of ethanol. The precipitated salt is filtered, washed with ethanol and dried to obtain 20.7 gm of the soluble calcium salt of hydroxycitric acid (yield 89.84%).

EXAMPLE 3

An anion exchange resin (bed volume IL) was loaded onto a glass column and washed thoroughly with 10% aqueous sodium hydroxide to remove the chloride present in the resin. The column was then washed with water till the eluate pH was neutral. Three hundred milliliters of an aqueous solution containing 108 gm of (−) hydroxycitric acid was loaded onto the column and washed with water to remove the colored materials. The column was eluted with 1 liter of an aqueous solution containing 63 gm of sodium hydroxide followed by 0.5 L of water. The combined eluate (1.5 liters) containing sodium salt of hydroxycitric acid was divided into two parts (750 ml each) and the soluble calcium salt was prepared as follows.

a) A portion of the sodium salt of hydroxycitric acid (750 ml) was concentrated to 200 ml. Fifty milliliters of a solution containing 20.25 gin of calcium chloride was added drop wise with vigorous stirring. The soluble salt of hydroxycitric acid thus formed was precipitated by the addition of ethanol, collected by filtration, washed with ethanol and dried to obtain 60.3 gm of the soluble calcium salt of hydroxycitric acid (yield: 91.8%).

b) The remaining portion of the eluate (750-ml) from the anion exchange column was passed through a column of cation exchange resin (bed volume 750 ml). The column was washed with water until the pH of the eluent reached neutral. One liter of the flow through which contained 45 gm of free (−) hydroxycitric acid was collected, concentrated in Vacuo to 100 ml and reneutralized by the addition of 27 gm of sodium hydroxide pellets. To the resultant solution of the sodium salt of (−) hydroxycitric acid, 50 ml of a solution containing 18 gm of calcium chloride was added drop wise with vigorous sting. The resultant soluble calcium salt of hydroxycitric acid was precipitated by the addition of ethanol. The precipitated salt was filtered, washed with ethanol and dried to obtain 54 gm of the soluble calcium salt of (−) hydroxycitric acid (yield: 93.75%).

EXAMPLE 4

One hundred milliliters of 48% enriched aqueous solution of (−) hydroxycitric acid solution was evaporated 670 C. in vacuo to remove water. The syrup thus formed was transferred into petridishes dried and desiccated under vacuum for 4–5 hours. The solid lactone of hydroxycitric acid weighing 30.6 gm was collected. To the said lactone residue, 60 ml of a solution containing 18 gm of sodium hydroxide was added. To the resultant solution of the sodium salt of (−) hydroxycitric acid, 30 ml of a solution containing 12.6 gm of calcium chloride was added drop wise with vigorous stirring. The soluble salt of hydroxycitric acid is then precipitated by addition of ethanol. The precipitated salt was filtered, washed with ethanol and dried to obtain 36 gm of the soluble calcium salt of hydroxycitric acid (yield: 91.91%).

This invention also provides the use of the said soluble double metal salt of group IA and IIA of (−) hydroxycitric acid of formula I and particularly formula II in beverages and other food products.

Beverages containing 0–15 weight % alcohol and syrups including soluble double metal salt of group IA and IIA of (−) hydroxycitric acid of formula I or formula II in the proportion 0.01–10% w/v.

The said beverage is a Pilsner beer containing alcohol content 3.0–3.8 weight % or Dortmund beer containing alcohol content 2.5–4.0 weight % or Munich beer containing alcohol content 2.0–5.0 weight % or Munich Ale or Porter beer containing alcohol contents 2.0–5.0 weight % or Stout beer containing alcohol content 5.0–6.5 weight %, each said beer includes the soluble double metal salt of group IA or IIA of formula I or II in the proportion 0.01–0.5% w/v.

The said beverage is aerated or non-aerated beverage/colas and the syrups are either processed or naturally occurring like honey including soluble double metal salt of group IA and IIA of (−) hydroxycitric acid of formula I or II in the proportion 0.01–10% w/v.

Soluble double metal salt of group IA and IIA of (−) hydroxycitric acid of formula I or formula II in the proportion 0.01–10% w/v is added at any stage during the production of the beverage or processed syrups.

We claim:

1. A new soluble double metal salt of group IA and IIA of (−) hydroxycitric acid of general formula I as given below:

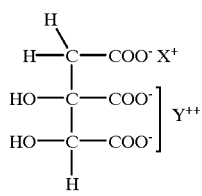

Formula I where X is IA group metal: Li or Na or K or Rb or Cs or Fr

Where Y is IIA group metal: Be or Mg or Ca or Sr or Ba or Ra where the concentration of X in the salt varies from 1.5–51.0%, the concentration of Y in the salts varies from 2.0–50.9% the concentration of HCA in the salt varies from 31.0–93.0% depending on the nature of X and Y.

2. The new soluble double metal salt of group IA and IIA of (−) hydroxycitric acid as claimed in claim 1, wherein X is Na$^+$ and Y is Ca$^{++}$, Concentration of sodium in the salt: 8.58%

Concentration of calcium in the salt: 14.92%

Concentration of (−) hydroxycitric acid: 76.50%.

3. A process of preparing soluble double metal salt of group IA and IIA of (−)hydroxycitric acid of general formula 1 as claimed in claim 1, comprising:

i.) preparing (−)hydroxycitric acid liquid concentrate/solid lactone of hydroxycitric acid from Garcinia extract, ii) neutralizing free (−)hydroxycitric acid present in said liquid concentrate/lactone (−)hydroxycitric acid with group IA metal hydroxide;

iii) displacing partially the group IA metal salt ions at both secondary and tertiary carbon positions in the salt solution obtained in step (ii) by adding group IIA metal chloride at an acidic pH, leaving primary carbon position intact, to form soluble double metal salt of group IA and IIA of (−)hydroxycitric acid; then iv) precipitating said solubilized double metal salt by adding an aqueous polar solvent to isolate said soluble double metal salt of group IA and IIA of (−)hydroxycitric acid.

4. The process as claimed in claim 3, wherein the preparation of (−)hydroxycitric acid concentrate from the Garcinia extract further comprises:

i) treating said Garcinia extract with group IA metal hydroxide to obtain soluble group IA metal salt of (−)hydroxycitric acid;

ii) displacing completely said group IA metal ion with group IIA metal ion by adding group IIA metal chloride solution at an acidic pH to precipitate insoluble group IIA metal salt of (−)hydroxycitric acid;

iii) collecting the precipitated insoluble group IIA metal salt of (−)hydroxycitric acid and washing it with water; then iv) adding a water soluble organic acid to said precipitated insoluble salt to form a insoluble salt of group IIA metal and releasing pure (−)hydroxycitric acid; then v) repeating the steps (iii) and (iv) to obtain a concentrate of (−)hydroxycitric acid; and vi) decolorizing the hydroxycitric acid concentrate, if desired.

5. The process as claimed in claim 4 wherein the said water soluble organic acid is an oxalic acid.

6. The process as claimed in claim 3 wherein partial displacement of group IA metal ion in step 3 is carried out with one equivalent of group IIA metal chloride.

7. The process as claimed in claim 3 wherein group IA metal hydroxides used are LiOH, NaOH, RbOH, CsOH and FrOH and group IIA metal chlorides used are BeCl$_2$, MgCl$_2$, CaCl$_2$, SrCl$_2$, BaCl$_2$ and RaCl$_2$.

8. The process as claimed in claim 3 wherein the said polar solvents are methanol, ethanol, propanol, isopropanol and acetone.

9. The process as claimed in claim 3 wherein the aqueous polar solvent is 80% acetone in water.

10. The process as claimed in claim 1 wherein soluble group IIA metal salt of (−) hydroxycitric acid is soluble calcium salt of (−) hydroxycitric acid.

* * * * *